US00PP23052P2

(12) United States Plant Patent
Miedema-Jorna

(10) Patent No.: US PP23,052 P2
(45) Date of Patent: Sep. 18, 2012

(54) **NEW GUINEA *IMPATIENS* PLANT NAMED 'FIDIMPREDMI'**

(50) Latin Name: *Impatiens hawkeri*
Varietal Denomination: Fidimpredmi

(75) Inventor: Anita Miedema-Jorna, De Lier (NL)

(73) Assignee: Fides B.V., De Lier (NL)

( * ) Notice: Subject to any disclaimer, the term of this patent is extended or adjusted under 35 U.S.C. 154(b) by 74 days.

(21) Appl. No.: 12/927,942

(22) Filed: Nov. 30, 2010

(51) Int. Cl.
*A01H 5/00* (2006.01)

(52) U.S. Cl. ..... Plt./318.1

(58) Field of Classification Search ..... Plt./318.1, Plt./318.7
See application file for complete search history.

*Primary Examiner* — June Hwu
(74) *Attorney, Agent, or Firm* — C. A. Whealy

(57) ABSTRACT

A new and distinct cultivar of *Impatiens* plant named 'Fidimpredmi', characterized by its upright and outwardly spreading growth habit; mounded plant form; freely branching habit; dark green-colored leaves; freely flowering habit; large red-colored flowers with a white-colored star-shaped pattern; and good garden performance.

1 Drawing Sheet

Botanical designation: *Impatiens hawkeri*.
Cultivar denomination: 'FIDIMPREDMI'.

BACKGROUND OF THE INVENTION

The present invention relates to a new and distinct cultivar of New Guinea *Impatiens* plant, botanically known as *Impatiens hawkeri* and hereinafter referred to by the name 'Fidimpredmi'.

The new *Impatiens* plant is a product of a planned breeding program conducted by the Inventor in De Lier, The Netherlands. The objective of the breeding program is to create new freely-branching New Guinea *Impatiens* plants with freely flowering habit and large attractive and uniquely colored flowers.

The new *Impatiens* plant originated from a cross-pollination made in 2006 by the Inventor in De Lier, The Netherlands of two unnamed proprietary selections of *Impatiens hawkeri*, not patented. The new *Impatiens* plant was discovered and selected by the Inventor as a single flowering plant within the progeny of the stated cross-pollination in a controlled environment in De Lier, The Netherlands.

Asexual reproduction of the new *Impatiens* plant by vegetative cuttings in a controlled environment in De Lier, The Netherlands since 2008, has shown that the unique features of this new *Impatiens* plant are stable and reproduced true to type in successive generations.

SUMMARY OF THE INVENTION

Plants of the new *Impatiens* plant have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Fidimpredmi'. These characteristics in combination distinguish 'Fidimpredmi' as a new and distinct cultivar of *Impatiens* plant:

1. Upright and outwardly spreading growth habit; mounded plant form.

2. Freely branching habit.
3. Dark green-colored leaves.
4. Freely flowering habit.
5. Large red-colored flowers with a white-colored star-shaped pattern.
6. Good garden performance.

Plants of the new *Impatiens* can be compared to plants of the female parent selection. Plants of the new *Impatiens* differ primarily from plants of the female parent selection in the following characteristics:

1. Plants of the new *Impatiens* are not as compact as plants of the female parent selection.
2. Flowers of plants of the new *Impatiens* and the female parent selection differ in flower color as flowers of plants of the female parent selection are pale red in color and do not have a star-shaped pattern.

Plants of the new *Impatiens* can be compared to plants of the male parent selection. Plants of the new *Impatiens* differ primarily from plants of the male parent selection in the following characteristics:

1. Plants of the new *Impatiens* are more freely branching than plants of the male parent selection.
2. Flowers of plants of the new *Impatiens* and the male parent selection differ in flower color as flowers of plants of the male parent selection are red in color and do not have a star-shaped pattern.

Plants of the new *Impatiens* can be compared to plants of *Impatiens hawkeri* 'Tamar Red', not patented. In side-by-side comparisons conducted in De Lier, The Netherlands, plants of the new *Impatiens* differed primarily from plants of 'Tamar Red' in the following characteristics:

1. Plants of the new *Impatiens* had larger flowers than plants of 'Tamar Red'.
2. Flowers of plants of the new *Impatiens* and 'Tamar Red' differed in flower color as flowers of plants of 'Tamar Red' were red in color and did not have a star-shaped pattern.

BRIEF DESCRIPTION OF THE PHOTOGRAPH

The accompanying colored photograph illustrates the overall appearance of the new *Impatiens* plant showing the colors as true as it is reasonably possible to obtain in colored reproductions of this type. Colors in the photograph may differ slightly from the color values cited in the detailed botanical description which accurately describe the colors of the new *Impatiens* plant.

The photograph comprises a side perspective view of a typical flowering plant of 'Fidimpredmi' grown in a container.

DETAILED BOTANICAL DESCRIPTION

The aforementioned photograph and following observations, measurements and values describe plants grown in 12-cm containers in a glass-covered greenhouse in De Lier, The Netherlands under commercial practice with day and night temperatures averaging 18° C. Plants were ten weeks old when the photograph and description were taken. In the following description, color references are made to The Royal Horticultural Society Colour Chart, 2007 Edition, except where general terms of ordinary dictionary significance are used.

Botanical classification: *Impatiens hawkeri* 'Fidimpredmi'.

Parentage:

*Female, or seed, parent*.—Unnamed proprietary selection of *Impatiens hawkeri*, not patented.

*Male, or pollen, parent*.—Unnamed proprietary selection of *Impatiens hawkeri*, not patented.

Propagation:

*Type*.—By vegetative cuttings.

*Time to initiate roots, summer*.—About five to seven days at temperatures of 19° C. to 20° C.

*Time to initiate roots, winter*.—About six to eight days at temperatures of 19° C. to 20° C.

*Time to produce a rooted young plant, summer*.—About 14 to 19 days at temperatures of 19° C. to 20° C.

*Time to produce a rooted young plant, winter*.—About 14 to 21 days at temperatures of 19° C. to 20° C.

*Root description*.—Fine; white to brown in color.

*Rooting habit*.—Freely branching.

Plant description:

*Plant and growth habit*.—Upright and outwardly spreading growth habit; mounded plant form; freely branching habit with about six lateral branches; pinching is typically not required; moderately vigorous growth habit.

*Plant height*.—About 18 cm.

*Plant diameter*.—About 32 cm.

Lateral branch description:

*Length*.—About 12 cm.

*Diameter*.—About 8 mm.

*Internode length*.—About 3 cm.

*Strength*.—Moderately strong.

*Aspect*.—Initially upright to outwardly spreading.

*Texture*.—Smooth, glabrous.

*Color*.—Close to 183A.

Foliage description:

*Arrangement*.—Opposite or in whorls of about five; simple.

*Length*.—About 10 cm.

*Width*.—About 3.5 cm.

*Shape*.—Elliptic.

*Apex*.—Acute.

*Base*.—Attenuate.

*Margin*.—Serrate with ciliation.

*Texture, upper and lower surfaces*.—Smooth, glabrous; leathery; moderately glossy in luster.

*Venation pattern*.—Pinnate; arcuate.

*Color*.—Developing leaves, upper surface: Close to N146A to N146B. Developing leaves, lower surface: Close to N183B. Fully expanded leaves, upper surface: Close to 139A; venation, close to 139A. Fully expanded leaves, lower surface: Close to N147B; venation, close to 183A.

*Petiole*.—Length: About 2.5 cm. Diameter: About 3 mm. Texture, upper and lower surfaces: Smooth, glabrous. Color, upper and lower surfaces: Center, close to 182C; towards the edges, close to 183A.

Flower description:

*Flower type and flowering habit*.—Single rounded axillary flowers; freely flowering habit with about five flowers developing per lateral branch; flowers positioned above the foliage and typically face upright or outwardly.

*Fragrance*.—None detected.

*Natural flowering season*.—Year-round under greenhouse conditions; in the garden, continuous flowering from spring through the summer in The Netherlands; early flowering habit, plants begin flowering about ten weeks after planting.

*Flower longevity*.—Flowers last about ten days on the plant under greenhouse conditions; petals self-cleaning, gynoecium persistent.

*Flower size*.—Diameter: About 5 cm. Depth: About 1 cm.

*Flower buds*.—Length: About 1.5 cm. Diameter: About 1.3 cm. Shape: Ovoid; pointed. Color: Close to 185A and N34A.

*Petals*.—Quantity/arrangement: Five per flower in a single whorl. Length, banner petal: About 2.5 cm. Length, lateral and lower petals: About 3.5 cm. Width, banner petal: About 4.5 cm. Width, lateral and lower petals: About 2.5 cm. Shape, banner petal: Cordate. Shape, lateral and lower petals: Broadly cordate. Apex, banner petal: Mucronate. Apex, lateral and lower petals: Emarginate. Base, all petals: Attenuate. Margin, all petals: Entire. Texture, all petals, upper and lower surfaces: Smooth, glabrous. Color, banner petal: When opening, upper surface: Close to 45A; central longitudinal stripe towards the apex, close to N155B and towards the base, close to 38A. When opening, lower surface: Close to 187A; central longitudinal stripe, close to 45A and 43A. Fully opened, upper surface: Close to 45A; towards the apex, close to 46A; central longitudinal stripe, close to NN155D; with development, longitudinal stripes become closer to NN155A and subsequently, close to 161D surrounded with close to N200A and 186A. Fully opened, lower surface: Close to 187A; central longitudinal stripe, close to 46A, 45A and 43A. Color, lateral petals: When opening, upper surface: Close to 45A; central longitudinal stripe towards the apex, close to N155B and towards the base, close to 38A. When opening, lower surface: Close to 43B; central longitudinal stripe, close to 38B. Fully opened, upper surface: Close to 45A; central longitudinal stripe, close to NN155D or a mixture of NN155D and 38B; with development, longitudinal stripes become closer to NN155A and subsequently, close to 161D surrounded with close to N200A and 186A. Fully opened, lower surface: Close to 43B; center, close to 43D; central longitudinal stripe, close to NN155D or a mixture of NN155D and 38B. Color, lower petals: When opening, upper surface: Close to 45A; central longitudinal stripe towards the apex, close to N155B and towards the base, close to 38A. When opening, lower surface: Close to 43A; central longitudinal stripe, close to 38B. Fully opened, upper surface: Close to 45A; central longitudinal stripe, close to NN155D or a mixture of NN155D and 38B; with development, longitudinal stripes become closer to NN155A and subsequently, close to 161D surrounded with close to N200A and 186A. Fully opened, lower surface: Close to 43B to 43C; central longitudinal stripe, close to NN155D or a mixture of NN155D and 38B.

*Sepals*.—Quantity/arrangement: Three; one modified into an elongated spur. Length, spurred sepal: About 1.6 cm. Length, spur: About 3.5 cm. Length, lateral sepals: About 1.2 cm. Width, spurred sepal: About 1.5 cm. Diameter, spur: About 2 mm. Width, lateral sepals: About 6 mm. Shape, spurred sepal: Broadly ovate with elongated spur. Shape, lateral sepals: Ovate. Apex, all sepals: Apiculate. Base, all sepals: Cuneate. Margin, all sepals: Entire. Texture, all sepals, upper and lower surfaces: Smooth, glabrous. Color, spurred sepal: Upper surface: Towards the base, close to 56D; towards the margins, close to 43D; towards the apex, close to 139D. Lower surface: Close to 43A and 43C; towards the apex, close to 139D. Spur, upper and lower surfaces: Close to 185B. Color, lateral sepals: Upper surface: Close to 43C; towards the margins, close to 139D. Lower surface: Center, close to 43C; towards the margins, close to 59C; towards the apex, close to 139D.

*Peduncles*.—Length: About 5 cm. Diameter: About 2 mm. Angle: Mostly erect. Strength: Moderately strong. Texture: Smooth, glabrous. Color: Close to 195A.

*Reproductive organs*.—Stamens: Quantity: Five fused at anthers; filaments free. Anther length: About 2 mm. Anther color: Close to 43B to 43C. Pollen amount: Moderate. Pollen color: Close to N155A. Pistils: Quantity per flower: One. Pistil length: About 0.4 mm. Stigma shape: Capitate. Stigma color: Close to 158C. Ovary color: Close to 144A.

*Seed/fruit*.—Seed and fruit production have not been observed.

Disease/pest resistance: Plants of the new *Impatiens* have not been observed to be resistant to pathogens and pests common to New Guinea *Impatiens*.

Garden performance: Plants of the new *Impatiens* have been observed to have good garden performance and tolerate wind, rain and temperatures ranging from about 4° C. to about 35° C.

It is claimed:

1. A new and distinct *Impatiens* plant named 'Fidimpredmi' as illustrated and described.

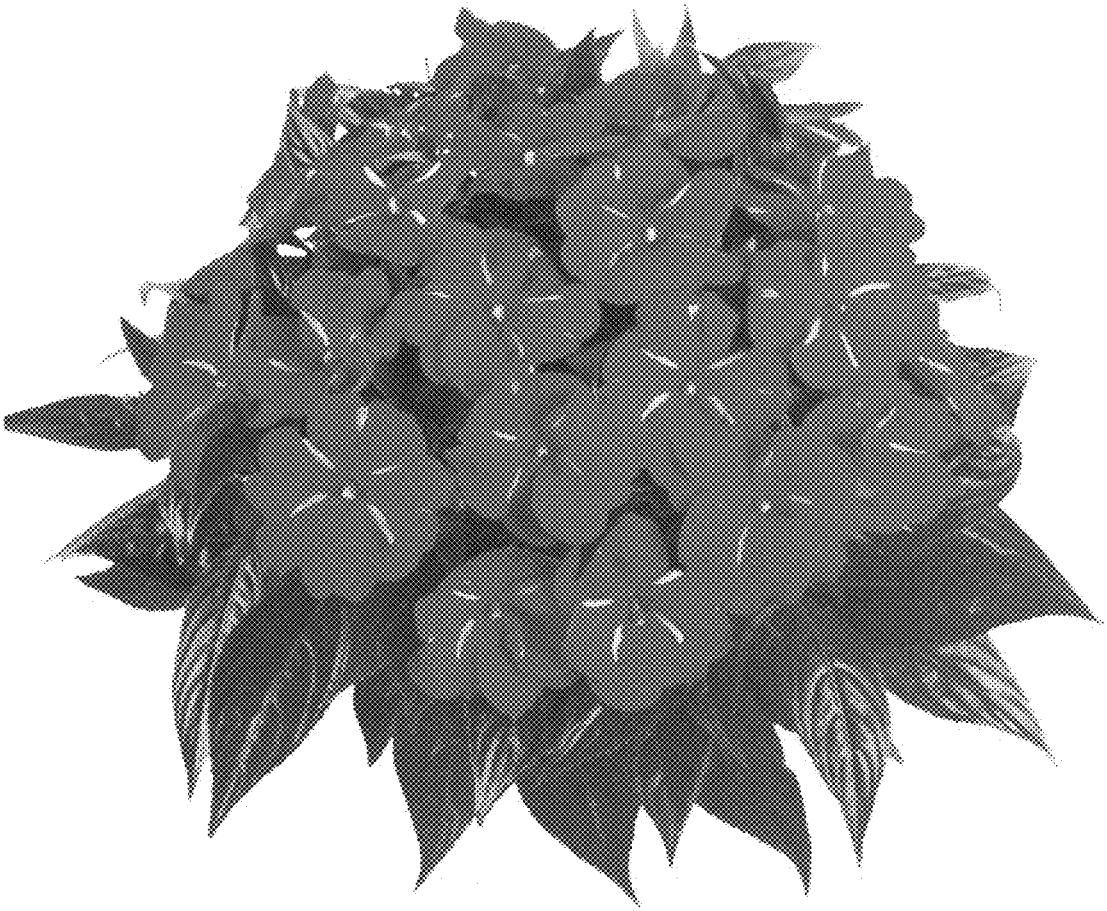

* * * * *